United States Patent [19]
Dobbs et al.

[11] Patent Number: 5,680,427
[45] Date of Patent: Oct. 21, 1997

[54] NORMALIZATION OF TOMOGRAPHIC IMAGE DATA

[75] Inventors: John Dobbs, Hamilton; Hans Weedon, Salem, both of Mass.

[73] Assignee: Analogic Corporation, Peabody, Mass.

[21] Appl. No.: 677,192

[22] Filed: Jul. 9, 1996

Related U.S. Application Data

[63] Continuation of Ser. No. 343,248, Nov. 22, 1994, abandoned.

[51] Int. Cl.<sup>6</sup> ................................................. G01N 23/00
[52] U.S. Cl. ........................................... 378/19; 378/4
[58] Field of Search .................................................. 378/19

[56] References Cited

U.S. PATENT DOCUMENTS 3,778,614  12/1973  Hounsfield ............................ 378/19
4,145,610  3/1979  Perilhou .
4,547,893  10/1985  Gordon .
4,769,827  9/1988  Uno et al. .
4,991,189  2/1991  Boomgaarden et al. .
5,228,069  7/1993  Arenson et al. .

*Primary Examiner*—Craig E. Church
*Attorney, Agent, or Firm*—Lappin & Kusmer LLP

[57] ABSTRACT

A monitoring detector assembly is positioned outside the scanning plane of a CT scanner to insure detection of unattenuated X-rays from the X-ray source of the scanner. The monitoring detector assembly preferably provides a sequence of monitor detection measurements simultaneously with the sequential acquisition of the image data during each projection of the scan by a filtered CT scanner. The image data are normalized using the closest in time monitor detection measurement.

21 Claims, 10 Drawing Sheets

NORMALIZATION OF TOMOGRAPHIC IMAGE DATA

This is a continuation of application Ser. No. 08/343,248 filed on Nov. 22, 1994 now abandoned.

RELATED APPLICATIONS

This application is related to co-pending U.S. patent application Ser. No. 08/343,248, entitled X-RAY FOCAL SPOT MOVEMENT COMPENSATION APPARATUS, filed in the names of John Dobbs and Ruvin Deych contemporaneously herewith and assigned to the present assignee (Attorney's Docket Number ANA-56).

FIELD OF THE INVENTION

This invention relates generally to improving the quality of tomographically scanned images, and more particularly to using readings of X-ray exposure taken during a CT (computer assisted tomography) scan to normalize image data derived from that scan.

BACKGROUND OF THE INVENTION

CT scanners of the third generation type include an X-ray source and X-ray detector system secured respectively on diametrically opposite sides of an annular-shaped disk. The latter is rotatably mounted within a gantry support so that during a scan the disk continuously rotates about a rotation axis while X-rays pass from the source through an object positioned within the opening of the disk to the detector system.

The detector system typically includes an array of detectors disposed as a single row in the shape of an arc of a circle having a center of curvature at the point, referred to as the "focal spot," where the radiation emanates from the X-ray source. The X-ray source and array of detectors are all positioned so that the X-ray paths between the source and each detector all lie in the same plane (hereinafter the "slice plane" or "scanning plane") normal to the rotation axis of the disk. Because the ray paths originate from substantially a point source and extend at different angles to the detectors, the ray paths resemble a fan, and thus the term "fan" beam is frequently used to describe all of the ray paths at any one instant of time. The X-rays that are detected by a single detector at a measuring instant during a scan is considered a "ray." The ray is partially attenuated by all the mass in its path so as to generate a Single intensity measurement as a function of the attenuation, and thus the density of the mass in that path. Projections or views, i.e., the X-ray intensity measurements, are typically done at each of a plurality of angular positions of the disk. As an example, a scanner may take 2880 projections during a single scan lasting roughly two seconds, with 384 data readings taken for each projection with a data acquisition system (DAS).

An image reconstructed from data acquired at all of the projection angles during the scan will be a slice along the scanning plane through the object being scanned. In order to "reconstruct" a density image of the section or "slice" of the object within the "field of view" in the defined scanning plane, the image is typically reconstructed in a pixel array, wherein each pixel in the array is attributed a value representative of the attenuation of all of the rays that pass through its corresponding position in the scanning plane during a scan. As the source and detectors rotate around the object, rays penetrate the object from different directions, or projection angles, passing through different combinations of pixel locations. The density distribution of the object in the slice plane is mathematically generated from these measurements, and the brightness value of each pixel is set to represent that distribution. The result is an array of pixels of differing values which represents a density image of the slice plane.

In order to produce a good quality image, the CT scanner designer works hard to minimize sources of error. Accordingly, steps are usually taken to provide for correction of errors either through design or calibration. For example, at zero X-ray levels it is important to minimize and stabilize signal offsets so that any measurement will contain a known constant offset for which corrections can be made. In addition, X-rays are provided at full scale and measurements are taken so as to generate "air" data with no absorbent material in the path of the X-rays so as to minimize errors due to drift in gain and measurement uncertainty at full scale. Two points of reference are thus provided between which data is corrected. In between these two points representing zero and full scale there is a curve which represents the relationship between X-ray levels and data values. The non-linear relationship between X-ray levels and data values results because the electrical signal varies in a non-linear manner with signal strength. Accordingly, materials of known absorption Values (e.g., water, polyethylene, polyvinyl chloride, etc.) of predetermined thicknesses are placed within the path of the fan beam and data are generated in order to calibrate the system. The data will represent points on the curve. Using these known materials allows for the determination of the correct dosage level for a particular scan, and detector efficiency. A best fit polynomial can be easily determined using known techniques so that a look up table can be generated and stored.

Within the context of insuring good tomographic images, it is also important that the data represent identical detection for all of the detectors for any given number of photons. If one datum, representative of a number of photons received during the measurement period from one detector is different from the data received from all of the other channels for the same measurement, the result will be an artifact in the reconstructed image. Thus, steps have been taken in the past to calibrate the offset and gain of each data channel so that errors attributed to these two factors are minimized.

Additional errors are attributable to the source of X-rays. Even though an X-ray tube is set to provide a constant X-ray flux output, the number of photons striking the detectors within a prescribed period of time can vary from detector to detector. As mentioned above, it is also known that each photon contributes to noise. Thus, the fewer number of photons detected, the poorer the signal-to-noise ratio (S/N).

In addition, the X-ray source may fluctuate during the scan, particularly as it reaches the end of its "life", producing fluctuating intensities of the X-rays; and in at least one case even though the X-ray source is set to provide a given number of photons for each view, the signal can be degraded. In some CT scanners called "filtered" CT scanners, the problem of a varying signal-to-noise ratio during the time of a scan is even more of a problem since not all of the measurements taken for a particular view by the detectors of the array are taken at precisely the same time. Instead each detector is coupled to a filter so that the detectors are read in a predetermined sequence for each projection. See, for example, U.S. Pat. No. 4,547,893 issued Oct. 15, 1985 to Bernard M. Gordon, and U.S. Pat. No. 4,769,827 issued Sep. 6, 1988 to Uno, et al., (the "Uno, et at. Patent").

It is known to provide a pair of reference detectors respectively at opposite ends of the arcuate image detector array, such as shown in the Uno, et al. Patent, to provide reference signals by which the data signals provided during a view can be compared, i.e., normalized. The reference detectors are used to sense the X-ray levels once during each projection, the measurements being provided very close in time to the X-ray measurements by the detectors in the center of the array since these values are considered by the patentees to be more important than measurements by the detectors at the ends of the array. It is assumed that the X-rays detected by the reference detectors will always be unattenuated. Unfortunately, with this arrangement, an incorrectly positioned patient or patient support table can obstruct either or both of the reference detectors during one or more projections of a scan, resulting in incorrect data regarding the X-ray levels sensed by the reference detectors for those projections. In addition, the measurement by each reference detector during a projection spans a period of time equal to the entire time of the projection ($T_o$) less the time it takes to read the reference channel ($T_{rs}$). A similar period of time is used to measure and read all of the channels, with the cycle for each of the 502 channels (500 data channels and two reference channels) being staggered over 502 intervals for a single projection. Thus, the time during which each of the data signals is detected and read will be different from channel to channel for the 500 data channels with the same reference signal being used for all 500 data channels. Consequently, the data signals acquired most distant in time from the reference signals (presumably those signals detected by the outer detectors next to the reference detectors 1 and 502) will be less accurate than those (detectors in the center, presumably detectors 250 and 251) taken close in time to the measurements by the reference detectors 1 and 502.

OBJECTS OF THE INVENTION

It is a general object of the present invention to provide an apparatus for X-ray image data normalization in a CT scanner of the type described that significantly reduces or overcomes the problems of the prior art.

A more specific object of the present invention is to provide for the normalization of image data signals associated with each projection of a filtered CT scan so as to reduce the effects of time-dependent variations in signal on the image data signals.

Another specific object of the present invention is to monitor the X-ray exposure level of a CT scanner during a scan so as to provide a correction for variations in the X-ray intensity.

And another object of the invention is to provide for the normalization of the image data signals associated with each projection of a filtered CT scan, even when a patient under study or a patient support table is not positioned properly with respect to an image detector array.

And yet another object of the present invention is to provide more accurate data from a filtered CT scan than provided from the system described in the Uno, et al. Patent.

And still another object of the present invention is to provide an improved filtered CT scanner in which the effects of fluctuations of the X-ray flux on data acquired during a scan is reduced without the significant computational requirements.

And yet another object of the present invention is to provide an improved CT scanner in which rapid fluctuations of X-ray flux can be tolerated so as to extend the service life of an X-ray source.

Other objects of the present invention will in part be suggested and will in part appear hereinafter. The invention accordingly comprises the apparatus possessing the construction, combination of elements, and arrangement of parts, and the processes involving the several steps and the relation and order of one or more of such steps with respect to the others, all which are exemplified in the following detailed disclosure and the scope of the application, all of which will be indicated in the claims.

SUMMARY OF THE INVENTION

An improved CT scanner includes an X-ray source for generating X-rays during a tomographic scan; X-ray detection means for detecting X-rays emitted by the X-ray source during a tomographic scan; and tomographic scanning means for rotating at least the X-ray source about a scanned object during a tomographic scan. The scanner includes an improved system for and utilizes an improved method of monitoring the output flux of an X-ray source of the scanner.

In accordance with one aspect of the invention, a monitor detector assembly is disposed so as to intercept an unattenuated portion of the X-rays emitted by the X-ray source along a path separate from the ray path(s) between the source and the image data detector means, and preferably outside the scanning plane, during each view of a scan so that the monitoring signal is read free of any objects within the field of view of the scan.

In accordance with another aspect of the invention, in a filtered CT scanner the monitor readings are performed more than once during the sequential data measurements for each view of the scan in a predetermined sequence. Each of the data measurements of each view is preferably normalized as a function of the monitor reading accuracy closest in time to the data measurements so as to reduce time dependent variations in the signal of the image detector readings.

In a preferred embodiment, the monitor detector assembly includes a plurality of detectors, wherein a sum of the signals from the detectors represents each monitor reading so as to enhance the resolution of the monitor detection assembly.

BRIEF DESCRIPTION OF THE DRAWINGS

The invention will be more fully understood from the following detailed description, in conjunction with the accompanying figures, wherein.

DETAILED DESCRIPTION OF THE DRAWINGS

Figure 1:
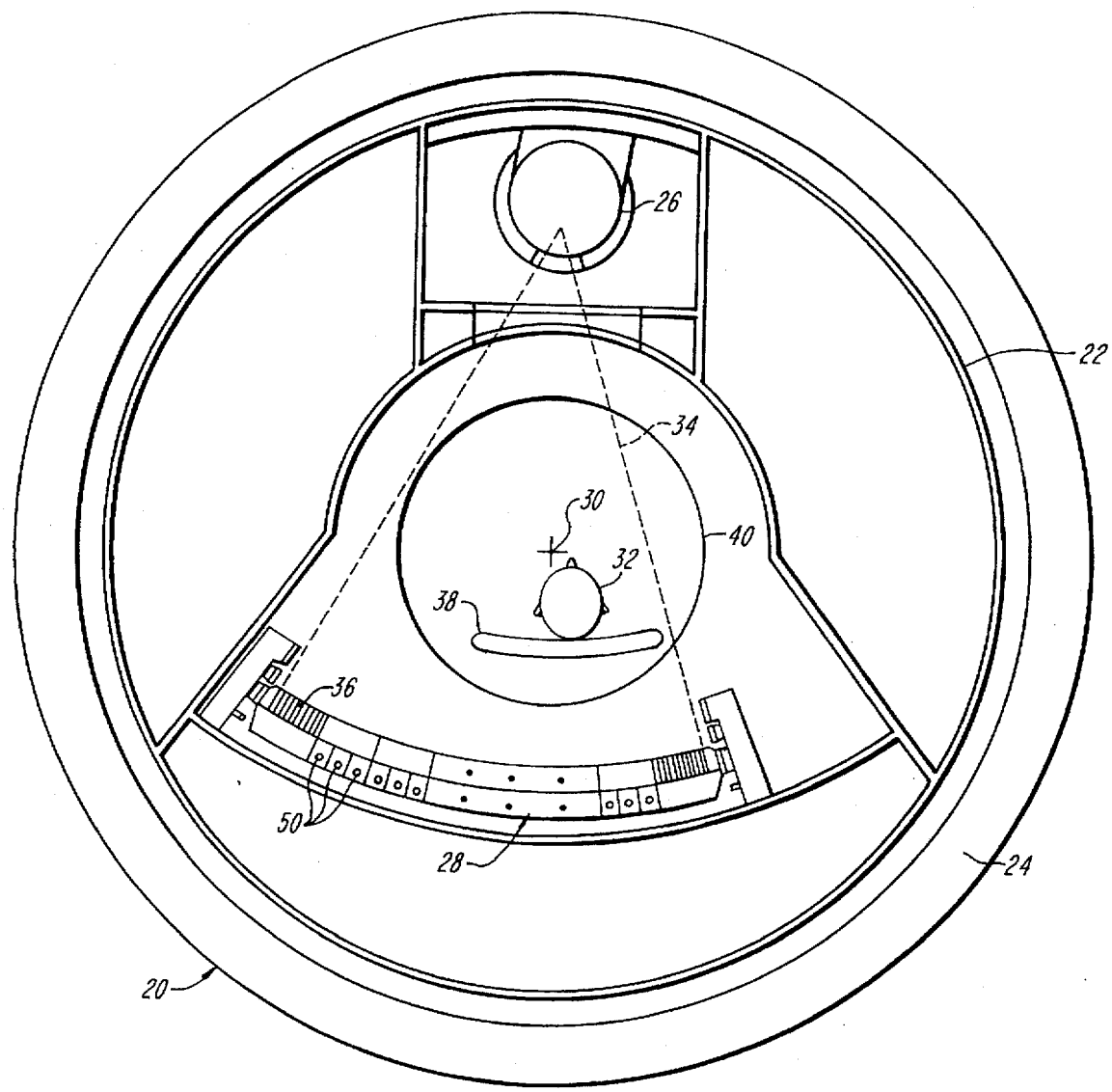
FIG. 1 is a simplified end view of a third generation filtered CT scanner including a monitor detector assembly provided in accordance with the present invention.
Figure 2:
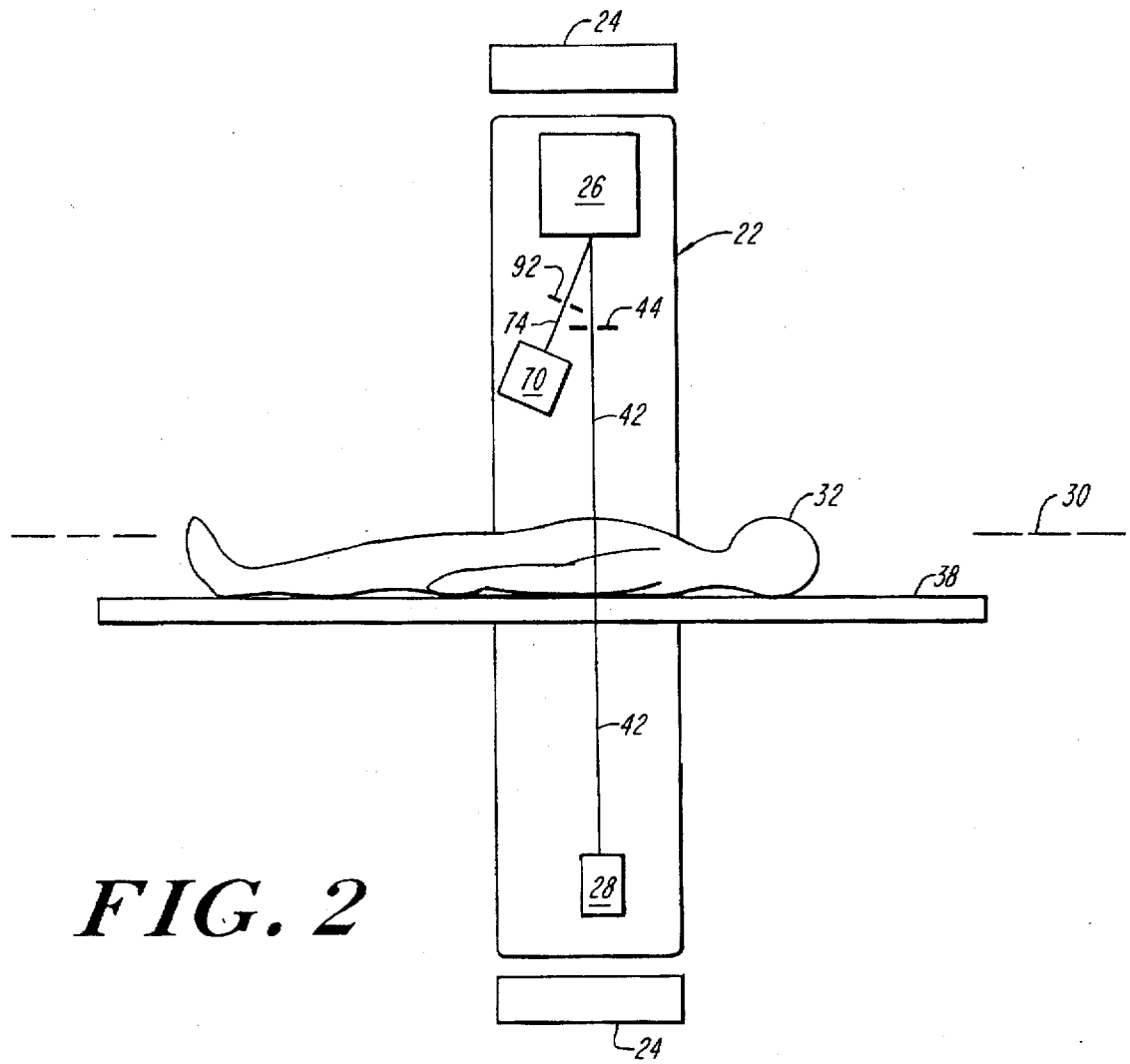
FIG. 2 is a simplified radial view of the filtered CT scanner shown in FIG. 1.

Referring to the drawings for a more complete understanding of the present invention, FIGS. 1 and 2 represent a filtered CT scanner 20 of the third generation type modified to incorporate the present invention. The system depicted in FIGS. 1 and 2 comprises a disk 22 mounted for rotation in a stationary gantry support 24. The disk 22 supports an X-ray source 26 and an arcuate image data detector array assembly 28 comprising a plurality of detectors 50. Source 26 and detector assembly 28 are rotated about rotation axis 30 (extending normal to the view shown in FIG. 1) so as to rotate around the object 32 that extends through the central opening of the disk during the CT scan. Object 32 may be a part of a live human patient, such as the head or torso. Source 28 emits radiation through a slit 44 (shown in FIG. 2) so as to define within a scanning plane (normal to rotation axis 30 and shown at 42 in FIG. 2), a continuous fan-shaped beam 34 of X-rays (seen in FIG. 1), which is sensed by the detectors of assembly 28 after passing through object 32. An array of anti-scatter plates 36 is located between object 32 and the detectors of assembly 28 to substantially prevent scattered rays from being sensed by the detectors. In the preferred embodiment the detectors number 384 and cover an arc of 48°, although the number and angle can vary. Disk 22, which may advantageously be of a light weight material, such as aluminum, is caused to rotate rapidly and smoothly around axis 30. The disk 22 is of an open frame construction so that object 32 can be positioned through the opening of the disk. Object 32 may be supported, for example, on a pallet or table 38, which of course, should be as transparent as practical to X-rays. As disk 22 rotates, detectors 50 of assembly 28 are periodically sampled, in a predetermined sequence to provide discrete measurements of X-rays passing in the scanning plane through object 32 from many projection angles. The measurements are then processed electronically with appropriate signal processing equipment (described hereinafter in connection with FIG. 3), in accordance with well-known mathematical techniques, so as to produce the final image information. The image information may then be placed in memory, analyzed in a computer, or suitably displayed. The final image will be one of the mass contained within the "field of view" of the scanner (as indicated by the circle 40 in FIG. 1) within the scanning plane (shown at 42 in FIG. 2). To the extent described, the system is the same as the one described in pending application, Ser. No. 08/190,945, filed Feb. 3, 1994 in the names of John Dobbs and David Banks for a MODULAR DETECTOR ARRANGEMENT FOR X-RAY TOMOGRAPHIC SYSTEM and commonly assigned to the present assignee.

In the preferred embodiment where assembly 28 comprises 384 data detectors, during each projection of the scan (which includes 2880 such views) the data detectors are sequentially read over a period of 576 microseconds, with each detector therefore being read within a 1.5 microsecond interval. At this speed of operation, computational requirements become important.

Figure 3:
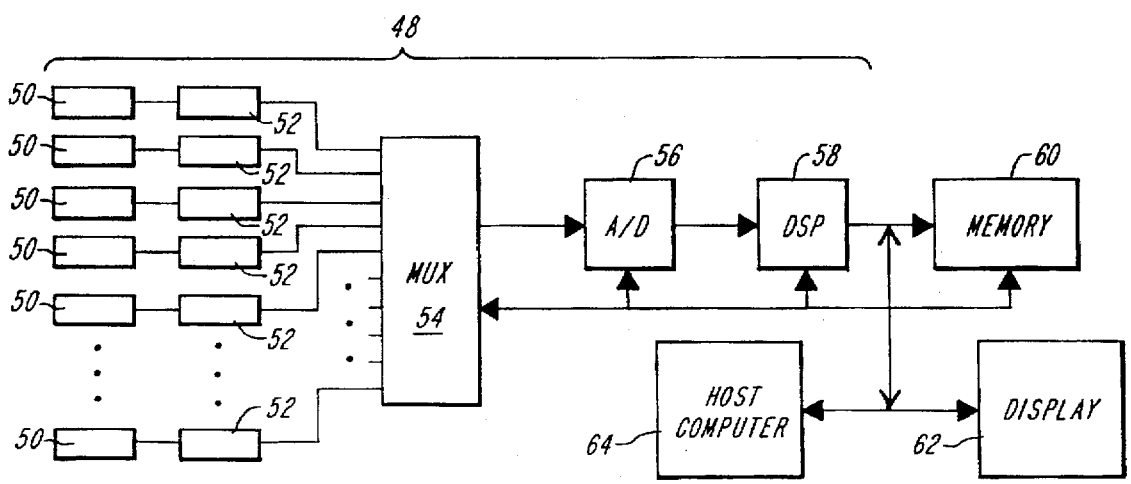
FIG. 3 is a block diagram of the image data detectors and the supporting electronics for the arcuate image detector array of FIGS. 1 and 2.

As shown in FIG. 3, each data detector 50 of detector array assembly 28, forms a part of the data acquisition system (DAS), generally indicated at 48. The DAS 48 further includes a preamplifier, low-pass filter and integrator 52 for amplifying, filtering and integrating the output of each detector for each projection. The output of each preamplifier, low pass filter and integrator 52 is connected to a multiplexer 54 of the DAS 48 for sequentially applying the signal outputs of the preamplifier, filter and integrator 52 to the input of an analog to digital (A/D) converter 56 of the DAS 48 for converting the analog signals to digital signals representative of the analog signals. The digital signal output of the A/D converter 56 is applied to a digital signal processor 58 of the DAS which stores the data in memory 60. The processor 58 includes a central processing unit (CPU) for controlling the operation of the components of the DAS 48, including the integration cycles of the preamplifier, low pass filter and integrator 52, in a manner which is well known. Memory 60 is large enough to store at least one complete set of data for an entire scan. The data can be retrieved and an image reconstructed and displayed on a display 62 in a manner which is well known. In this regard the memory preferably is also connected to a host computer 64, preferably provided with an array processor for reconstructing the image, and connected to display 62 for displaying the reconstructed image. In this case all of the detectors are connected to one multiplexer. It should be appreciated that the detectors can be divided into two or more groups, with the detectors of each group connected to its own multiplexer and A/D converter, and subsequently processed and stored. This increases the speed of operation at the expense of additional hardware.

Figure 4:
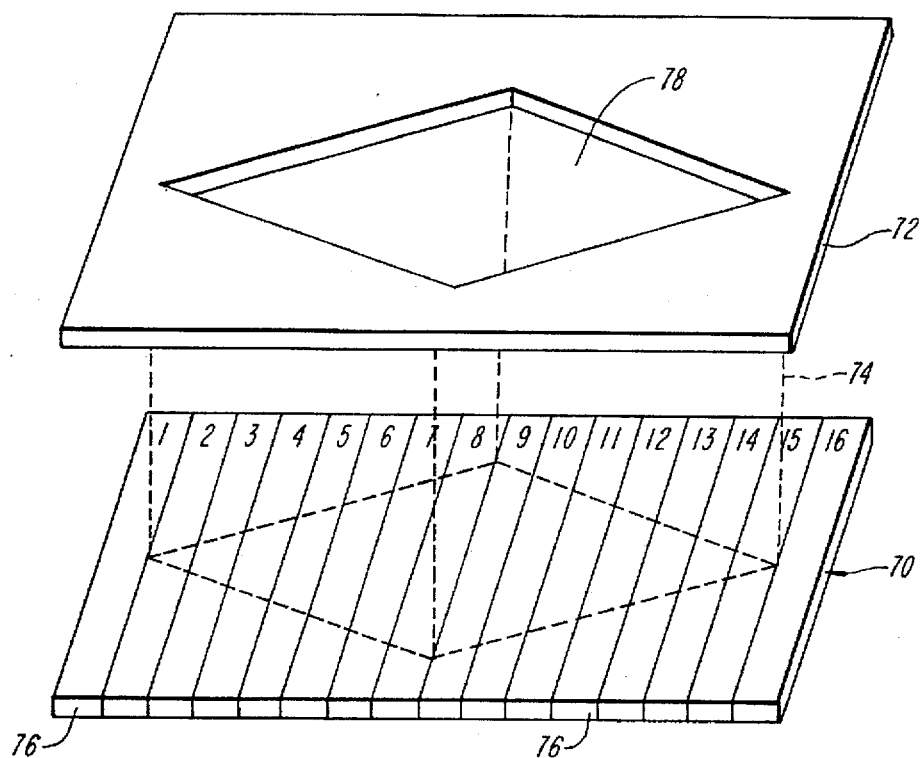
FIG. 4 is a simplified isometric view of the monitor detector assembly.

Referring to FIGS. 2 and 4, in accordance with one aspect of the present invention, a monitor detector assembly 70 for monitoring the output of the X-ray source 26 during each scan is placed outside the scanning plane 42, and thus the field of view 40 (shown in FIG. 1), so as to ensure that the monitor detector assembly 70 receives X-rays substantially unattenuated at full strength during each projection of each scan, regardless of what is placed and where it is placed within the field of view 40. Preferably, the monitor detector assembly 70 is fixed relative to the X-ray source 26 and rotates with the disk 22 at a position closer to the X-ray source 26 than the object 32. An aperture or slit defining element 72 defines a substantially unattenuated X-ray beam 74 between the source 26 and the monitor detector assembly 70. The monitor detector assembly 70 provides a signal representative of the X-ray flux detected by the monitor detector assembly only during preselected sampling intervals, when predetermined detector outputs of the detectors 50 of the detector array assembly 28 are read by the DAS 48 (shown in FIG. 3) for each projection.

In general the monitor detector assembly 70 is constructed and used so as to exploit a fundamental relationship of tomography. As shown in FIG. 4, when an object 32 is disposed within the scanning plane 42 within the "field of view" 40 and a scan is performed, X-rays are generated from the source 26 along the individual ray paths to the corresponding detectors 50. Those X-rays passing through the object 32 are partially attenuated by the object. The measurement of the partial attenuation by each detector along the corresponding ray path for each projection is determined by the ratio of the input X-ray intensity (i.e., the intensity detected by the corresponding detector 50 of interest) and the output X-ray intensity (i.e., the output of the source 26). Thus, for the kth channel:

$$\frac{I_{ko}}{I_k} = e^{-\int \mu dL} \qquad (1)$$

wherein $I_{ko}$ is the initial or output intensity of the source 26 used for the kth channel;

$I_k$ is the input intensity of the corresponding detector 50 for the kth channel after having traversed the corresponding ray path; and e is a constant that is the base for natural logarithms;

μ is the attenuation coefficient; and

L is the thickness of the material through which the X-rays pass along the corresponding ray path.

As described above, in the prior art $I_{ko}$ and $I_k$ are not measured simultaneously. $I_{ko}$ is measured when there is no object in the machine (air measurements), while $I_k$ is measured with the scanned object in the machine. The problem with this approach is that the source may not be emitting X-rays at the same rate when the two measurements are made. To resolve this problem, in accordance with one aspect of the present invention the monitor detector assembly 70 is used to measure the intensity of the X-ray output of the source 26 independently in both cases, i.e., for the air measurement and during a scan of an object 32. This results in the final relationship for the measured attenuation, normalized using the monitor readings as follows:

$$e^{-\int \mu DL} = \frac{I_{ko}(t_o)M_j(t_j)}{M_o(t_o)I_{kj}(t_j)} \qquad (2)$$

wherein $M_o(t_o)$ and $I_{ko}(t_o)$ are the intensity measurements made by the monitor assembly 70 and detector 50 of the kth channel during the air measurements taken during at time $t_o$;

$M_j(t_j)$ and $I_{kj}(t_j)$ are the intensity measurements made by the monitor assembly 70 and the detector 50 of the kth channel during the jth projection taken at time $t_j$.

Thus, in accordance with one aspect of the invention intensity measurements $I_{ko}(t_o)$, $M_o(t_o)$, $I_{kg}(t_j)$, and $M_j(t_j)$ are all taken over extended periods of time. The time intervals for each intensity measurement are chosen as a compromise between speed of data acquisition and quantum noise. Since the patient moves constantly, it is desirable to take the entire picture as quickly as possible. However, each datum in the data set associated with each intensity measurement is subject to the signal variations associated with the fact that the information comes in discrete X-ray quanta. Thus, from the point of view of noise, it is preferable to take as much time as possible to make each intensity measurement. The actual compromise is set by the rate at which X-rays are generated by the source 26, which in turn is defined by the cost, weight, and power of the X-ray tube and high voltage power supply used to power the X-ray tube of the source 26. The time for each projection is the time needed to detect enough of the X-rays to make a sufficiently noise free measurement. Thus, it is evident that each of the intensity measurements $I_o(t_o)$, $M_o(t_o)$, I(t) and M(t) in Equation (1) for each channel and for each projection are really integrals. For example, $$I_o(t_o) = \int_{t_o - \Delta t}^{t_o + \Delta t} F(t_o - g)I(g)d(g) \qquad (3)$$

wherein $F(t_o-g)$ is a filter function;

g is the time of arrival of a photon.

Similar expressions can be written for $M_o(t_o)$, I(t) and M(t).

The integration for each intensity measurement can be performed electronically by using an analog filter of a type well known for use in CT scanners as a part of each preamplifier, low pass filter and integrator 52, and preamplifier, low pass filter and integrator 80 (hereinafter described in connection with FIGS. 3 and 5) and which combines the charge for many quanta using a weighting function, i.e., $F(t_o-g)$, which is a function of the time difference between the time of arrival of a photon, i.e., "g", and the measurement time $t_o$. The measurement time $t_o$ is a known constant, before the time when the filtered signal is sampled. Each preamplifier, low pass filter and integrator 52 and 80 integrates the charge to give an integral of the signal identical to equation (3). The time interval 2Δt must be long enough to cover the function $F(t_o-g)$.

The relationship between $I_o(t_o)$ and $M_o(t_o)$ is geometric and electronic. It depends on the solid angle of the two detectors (i.e., the monitor detector and the detector of the array for the kth channel), the gain of the electronics for these two detectors, and the relative intensity of the X-rays in the two directions. These three factors, i.e., solid angle, gain and relative intensity, are made to be as constant as possible between the two measurement time intervals to and the time $t_k$. When the ratios of Equation (2) are taken, all of the factors cancel, so that $\int \lambda dL$ is truly being measured, not the variations of the operation of the machine over time.

There are certain assumptions made using this approach. It is assumed that the time over which the integration of each intensity measurement, I and M, is made is the same. Slight differences in measurement can be tolerated so long as there is no change in gain, solid angle, and intensity that has occurred between any two measurement times. To make sure that the above equations hold true, not only over long periods of time (from view to view) but also over a fraction of a single scan of the electronic readout system, the X-ray monitor detector assembly 70 is read many times (in the preferred embodiment eight times) for each view of the detector array, which is contrary to the prior art which at best was only concerned with X-ray monitor readings once per detector readout cycle, and not multiple monitor readings per readout cycle. Incorporating the present invention into a CT scanner results in much more rapid fluctuations in X-ray flux being tolerated. Rapid fluctuation in the X-ray intensity is a sign of "end of life" of an X-ray tube. Thus, by employing the present invention, it is possible to extend the life of the X-ray tube significantly.

As shown in greater detail in FIG. 4, the preferred monitor detector assembly 70 comprises a detector array of sixteen detectors 76 arranged side by side, and performs the function of monitoring (a) the alignment of the fan beam 34 (shown in FIG. 1), as described in co-pending application U.S. patent application Ser. No. 08/343,248, entitled X-RAY FOCAL SPOT MOVEMENT COMPENSATION APPARATUS, and filed in the name of John Dobbs and Ruvin Deych contemporaneously herewith (Attorney's Docket Number ANA-56), and (b) the intensity of the X-rays from the source 26 for normalizing the data in accordance with the present invention as described herein. The detectors 76 are preferably, but not necessarily, identical to the detectors 50 used to collect data. The slit defining element 72 is provided with a diamond-shaped aperture 78 so that when properly aligned with the monitor detector assembly 70, the diamond shaped beam strikes the detectors 76 so that the largest amount of flux falls on each of the center detectors eight and nine, no flux falls on the end detectors one and sixteen, and the amount of detected flux progressively increases from the detectors two and fifteen toward the center detectors eight and nine. As seen an equal amount of flux falls on the center pair of detectors eight and nine, an equal but lesser amount falls on each of the pair of detectors seven and ten, an equal but even smaller amount falls on each of the pair of detectors six and eleven, a still smaller and equal amount of flux falls on each of the two detectors five and twelve, etc.

Figure 5:
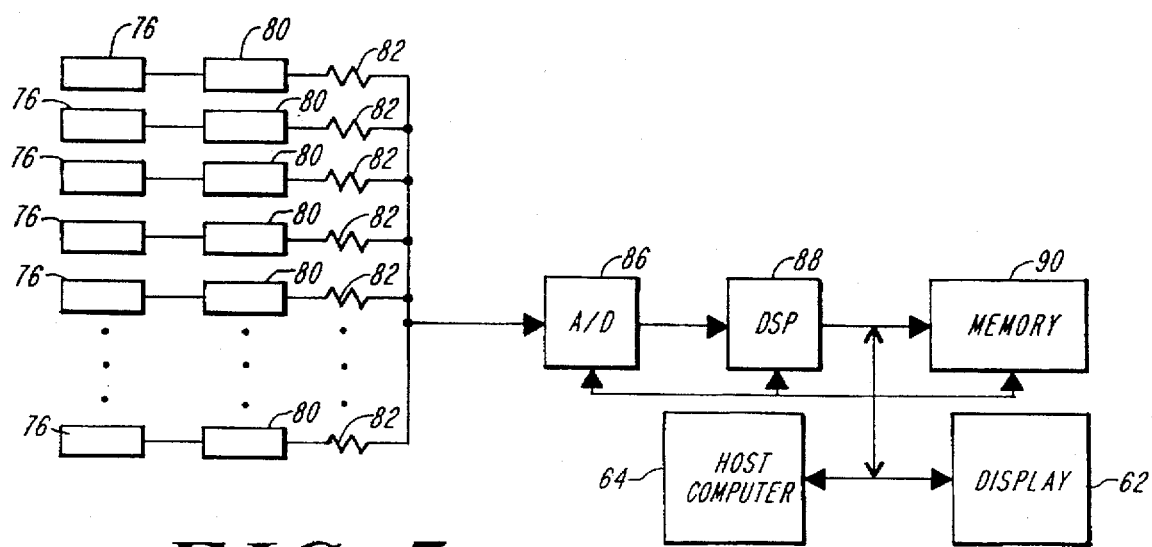
FIG. 5 is a block diagram of the monitor detectors and the supporting electronics for the monitor detector assembly designed in accordance with the present invention for use in the scanner of FIGS. 1 and 2.

Referring to FIGS. 3 and 5, each monitor detector 76 is connected to a preamplifier, low-pass filter and integrator 80, for example, which in turn is connected to a resistor 82 for generating a current to the summing node 84. The summing node provides a summed current signal with low statistical noise representative of a monitor reading of the unattenuated X-ray flux of the source 26. The summed signal will be independent of the position of beam 74 so long as the monitor assembly senses the entire beam 74. The greater the X-ray flux detected by the monitor detectors 76, the greater the summed signal at node 84. The summed signal provided at the node 84 is applied to the input of A/D converter 86, which in turn provides a digital output signal to the digital signal processor 88. The monitored data processed by processor 88 is stored in memory 90 and used to normalize the data collected during each projection of a scan according to the principles of the present invention. It should be appreciated that the processor 58 for processing the data signals and processor 88 for processing the monitored data can be provided by a single processor of a type well known in the art. Similarly, the memories 60 and 90 can be provided as a single random access memory (RAM) integrated circuit or set of such circuits. The data collected during each ray projection can be normalized as it is written into memory. However, where the process is a high speed operation, e.g., where each data detector 50 is read within a 1.5 microsecond interval, it is preferable that the data be normalized when reading data out of the memory 60 after the scan has been completed. The contents of the memories 60 and 90 are read by host computer 64 preferably for processing by the array processor and display 62.

It is understood that the monitor detectors 76 are each vulnerable to "damage" from incident X-ray flux, resulting in reduction of sensitivity. The damage is a slow process, and the resulting decline in sensitivity can be adequately compensated using a linear equation in the form of:

$$MON_c = K*D*MON \quad (4)$$

wherein $MON_c$ is the corrected monitor reading;
MON is the uncorrected monitor reading;
D dynamically depends on continuously updated and slowly varying characteristics of the CT scanner, such as the mean of the current readings of the power supply of the X-ray tube, the anode voltage of the X-ray tube, and the mean of the offset-corrected monitor reading taken over a similar time frame as the current and voltage measurements; and
K is an empirically determined constant.

According to another aspect of the invention, a plurality of monitor readings are taken and stored during air measurements (or more generally a material of known attenuation is placed within the field of view so as to provide a predetermined amount of attenuation) during each projection, i.e., during each complete sequential reading of the arcuate detector array assembly 28, and used to normalize the data received by detectors 50 during that sequential reading so as to provide more monitor readings per view than taught by Uno, et al. More particularly, in the preferred embodiment where each sequential reading corresponding to one of the 2880 ray projections takes 576 microseconds to read data from each of the detectors 50 into memory 60, monitor data is read into memory 90 at predetermined times during the 576 microseconds.

According to another aspect of the present invention, the normalization of the image data is achieved efficiently by taking a predetermined number of monitor readings in a predetermined sequence during each projection, and preferably using the monitored data reading closest in time to the time in which each detector data reading is acquired, i.e., the monitor reading that occurred most recently or will occur soonest, which ever represents the shortest period of time, to the data reading and dividing each image data reading by the nearest-in-time monitor reading. To determine which monitor reading occurred closest in time, a look-up table provided in host computer 64 can be used that associates each image detector reading with the closest-in-time monitor assembly reading.

Figure 6:
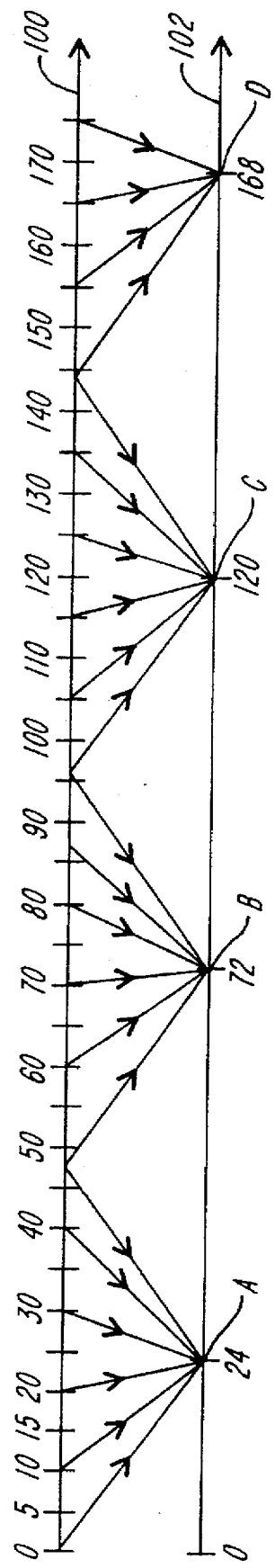
FIG. 6 is an example of a time-line diagram of a sequence of image detector readings and a sequence of monitor detector assembly readings during a projection reading, and a plurality of arrows illustrating which monitor assembly reading is optimally used for normalizing each image detector reading according to the invention.

Referring to FIG. 6, an example of the "closest in time" concept is illustrated. In the illustration, eight monitor readings are taken during the projection, equally spaced apart in time. A time line indicated at 100 represents a sequence of 384 image detector readings (of which only the first 175 are shown), and a second time line 102 represents a sequence of eight monitor readings (of which only the first four are shown). With eight monitor readings taken during the 384 data readings, the first monitor reading A is the closest in time to the first forty-eight image detector readings represented on the first time line 100. Likewise, the second monitor reading B is closest in time to the second forty-eight readings, i.e., readings forty-nine through ninety-six, and so forth regarding monitor readings. The first monitor reading is therefore taken during the 1.5 microsecond interval when the twenty-fourth data detector 50 reading is taken, while the last monitor reading (not shown) is taken during the 1.5 microsecond interval when the three hundred sixtieth data detector 50 reading is taken. The second through seventh monitor readings are taken during the 1.5 microsecond intervals when the seventy-second, one hundred twentieth, one hundred sixty eighth, two hundred sixteenth, two hundred sixty fourth, and three hundred twelfth data detector readings are respectively taken.

Ideally, the S/N ratio of each signal detected by each detector 50 should remain constant assuming a constant X-ray level from source 26. However, as discussed above, the S/N ratio decreases with time unless some form of normalization is employed.

Figure 7:
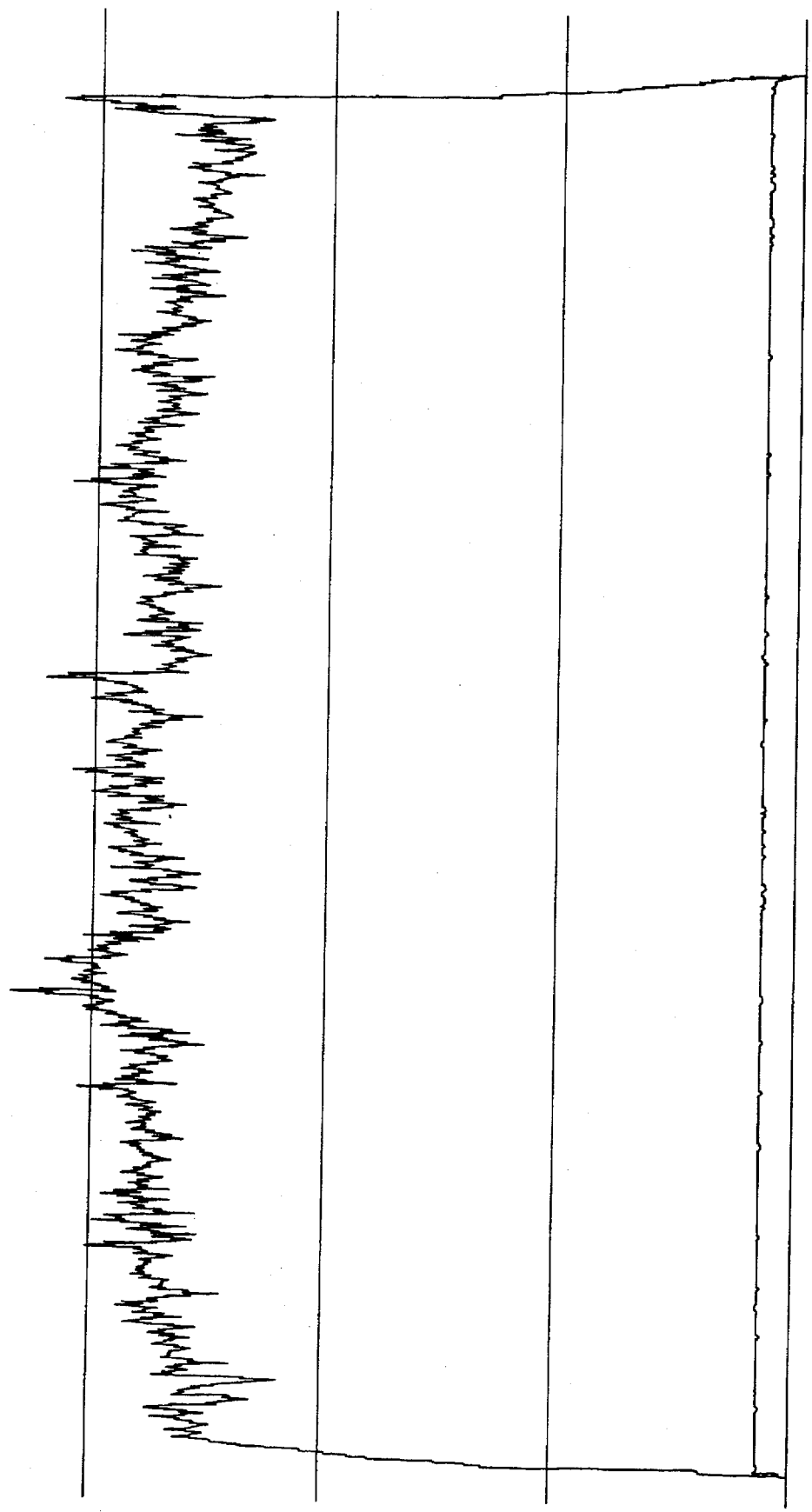
FIG. 7 is a graph of signal-to-noise ratio as a function of detector channel, where each image detector is exposed to full-scale fan-beam intensity, normalized using the "sliding window" method.

FIG. 7 shows how one normalization approach considered by us provides a relatively constant S/N ratio for all of the data readings. We call this approach the "sliding window" approach. This approach requires a monitor reading of the unattenuated value of the X-ray beam to be simultaneously taken for each detector reading during each view. Thus, where 384 detector readings are taken per view, 384 monitor readings are required. In order to normalize each image detector reading, the monitor reading of a predetermined number of previous readings and a predetermined number of subsequent readings are added together to provide a normalization factor for the current image detector reading. Thus, for example, using a sum of eight monitor readings in the sliding window method, during the ninth detector reading of the entire sequence of 384 readings of the detector array, the previous four monitor readings (when the fifth through eighth detector readings of the sequence occur) and the next four monitor readings (when the tenth through thirteenth detector readings of the sequence occur) are added so as to provide a normalization factor by which the ninth reading can be divided to normalize the ninth reading. In a similar manner, during the reading of the tenth detector reading of the entire sequence of readings of the detector array, the previous four monitor readings (when the sixth through ninth detector readings of the sequence occur) and the next four monitor readings (when the eleventh through fourteenth detector readings of the sequence occur) are added together so as to provide a normalization factor by which the tenth reading can be divided to normalize the tenth reading. To provide normalization, this approach thus uses a "sliding window" sum of eight monitor readings for each of the image detector readings of the entire array (for example, 384 detector readings) for a view. Thus, 384 sliding window sums must be computed for each projection. In this approach a relatively constant S/N ratio, acceptable within the limits of quantum noise, is provided. The graph shown in FIG. 7 was obtained by computation using an "artificial" monitor. However, the approach also requires substantial computations and additional hardware, which will significantly increase the cost of the scanner and severely limit the speed at which data is processed. This approach therefore provides good results, but the amount of processing time and additional hardware is unacceptable where speed in data acquisition is important.

Figure 8:
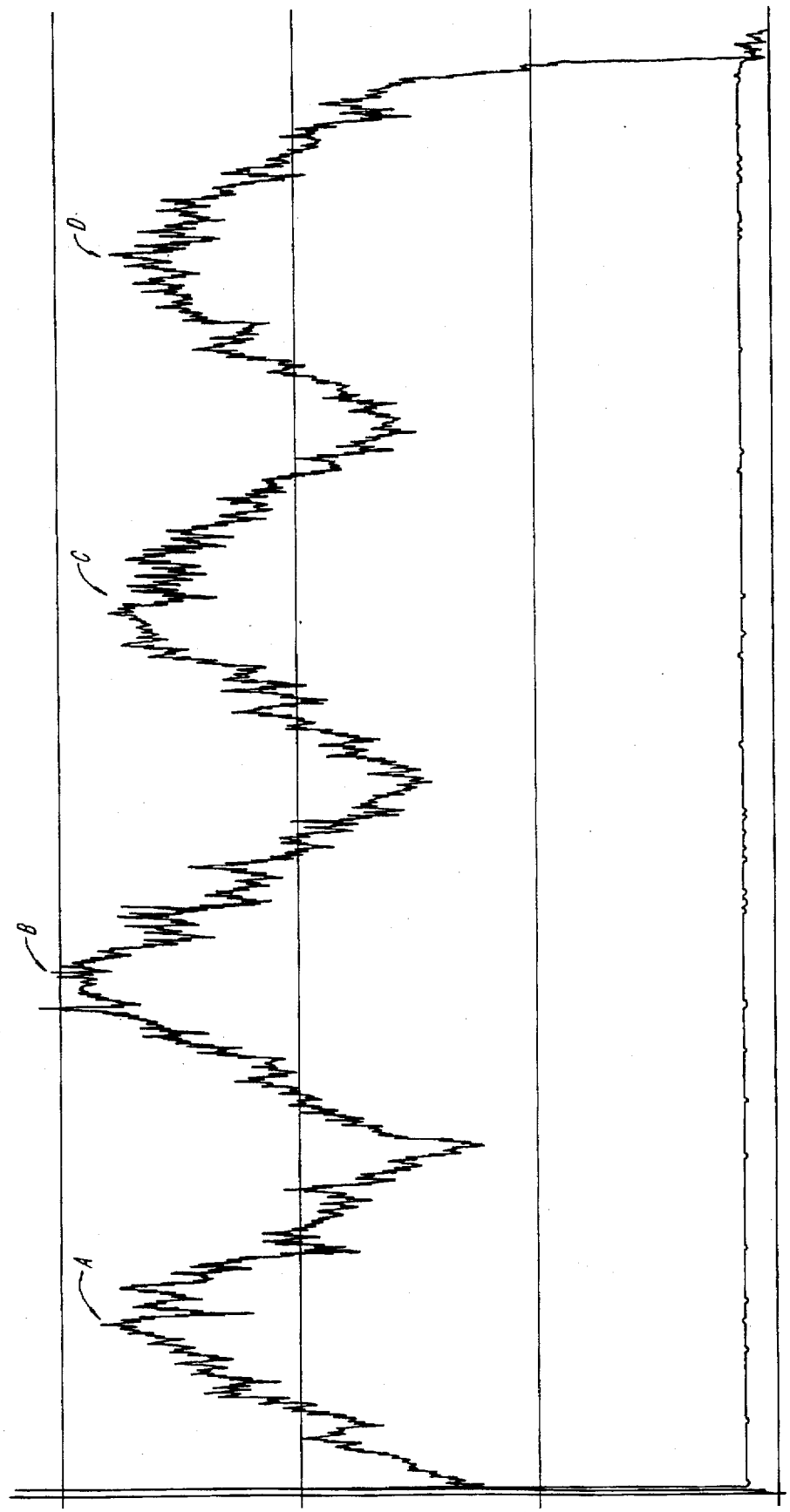
FIG. 8 is a graphical illustration of signal-to-noise ratio as a function of detector channel, where each image detector is exposed to full-scale fan-beam intensity and the resulting data is normalized in accordance with the preferred embodiment of the present invention in an example using the nearest of four monitor readings during each projected view.
Figure 9:
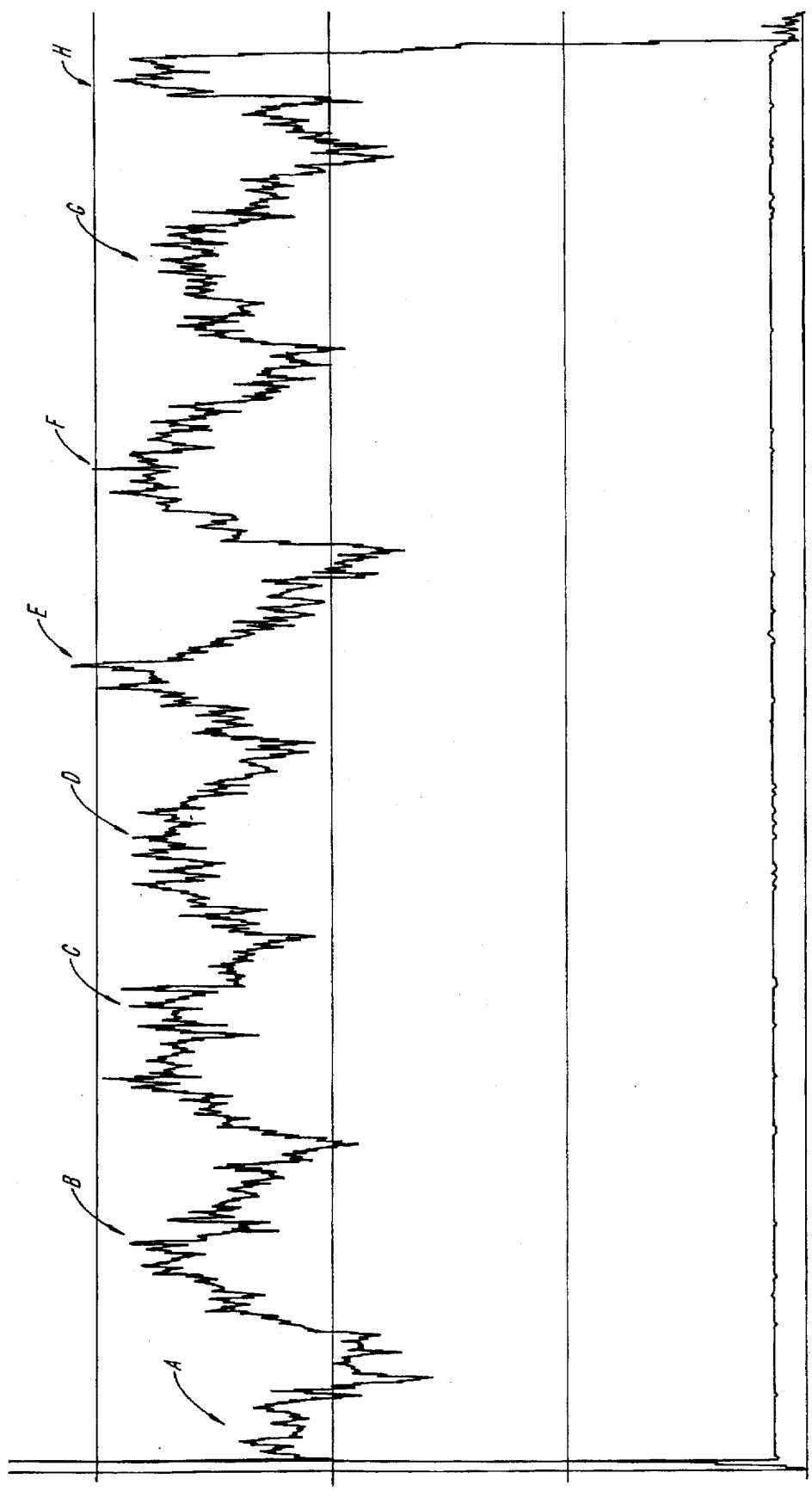
FIG. 9 is a graphical illustration of signal-to-noise ratio as a function of detector channel, where each image detector is exposed to full-scale fan-beam intensity and the resulting data is normalized in accordance with the preferred embodiment of the present invention in an example using the nearest of eight monitor readings during each view.
Figure 10:
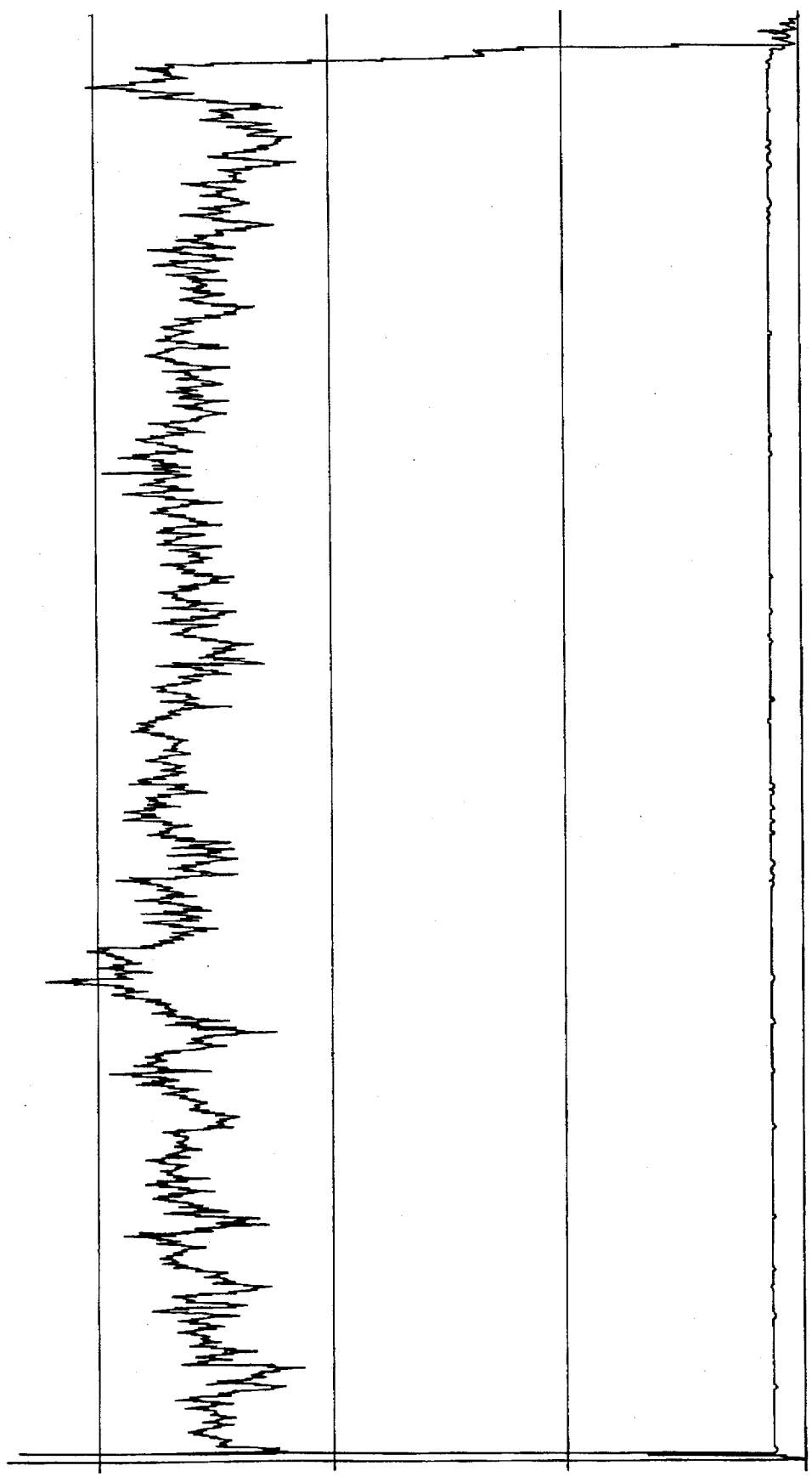
FIG. 10 is a graphical illustration of signal-to-noise ratio as a function of detector channel, where each image detector is exposed to full-scale fan-beam intensity and the resulting data is normalized in accordance with the preferred embodiment of the present invention in an example using the nearest of sixteen monitor readings during each view.

FIGS. 8–10 are graphs of S/N (signal-to-noise) ratio (in increments of 1000) as a function of detector channel (1–384), where each data detector 50 and monitor detector 76 is exposed to full-scale fan-beam intensity, i.e., no object was present in the field of view 40 that might absorb X-rays. FIG. 8 illustrates a nearest of four technique where only four equally spaced (in time) monitor readings are taken during the 384 data readings. FIGS. 9 and 10 illustrate nearest of eight and nearest of sixteen techniques, respectively where eight and sixteen monitor readings, equally spaced in time, are taken during the 384 data readings. It is clear that the S/N data of FIG. 8 exhibits four easily discernable peaks shown at A, B, C and D, when the monitor readings were made. Obviously as the intervals of data readings gets closer to an interval between adjacent peaks the S/N decreases because normalization becomes less reliable.

The S/N data of FIG. 9 exhibits eight less discernable peaks A–H. The eight peaks correspond to the eight monitor readings. For example, the image detector reading represented by peak B is the image detector reading that were taken closest in time to the second of eight monitor assembly readings. Note that the S/N ratio is lowest for image detector readings taken farthest in time from a detector monitor reading.

Thus, the closer in time that the image detector reading occurs to the monitor reading, the higher the S/N ratio of the image detector reading will be after normalization with the monitor reading. Moreover, it follows that to maximize the S/N ratio over all of the image detector readings in a view, the sum of the distance in time from each image detector reading to a monitor assembly reading must be reduced, i.e., more monitor readings are needed for each projection. To achieve this, the monitor readings should be equidistantly spaced from each other over time, and equal numbers of image detector readings must be associated with each monitor assembly reading, as illustrated in FIG. 6.

Referring to FIG. 10, a graph of S/N ratio is presented as in FIGS. 8 and 9, wherein sixteen monitor assembly readings are taken per ray projection. Although more computations are performed, the nearest-in-time approach is still significantly less computationally intensive than the sliding window approach. Note the similarity of the data of FIG. 10, and the data of FIG. 7 of the sliding window approach so that for the specific example the nearest of sixteen technique appears to be optimum. Thus, using significantly less computations than the prior art, the invention provides substantially a similar S/N ratio profile.

Figure 11:
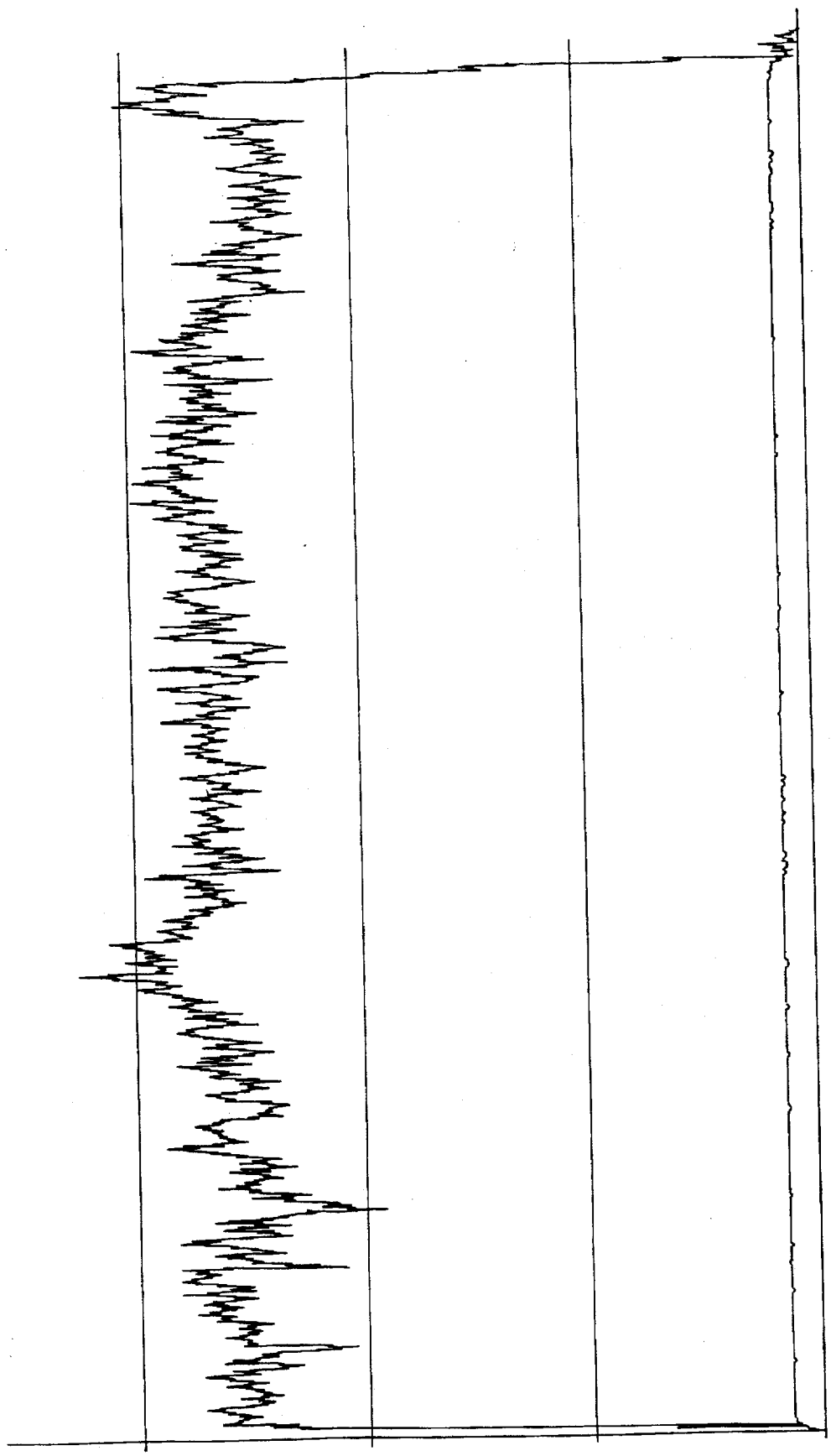
FIGS. 11 and 12 are graphical illustrations of signal-to-noise ratio as a function of detector channel, where each image detector is exposed to full-scale fan-beam intensity and the resulting data is normalized using an interpolation technique.
Figure 12:
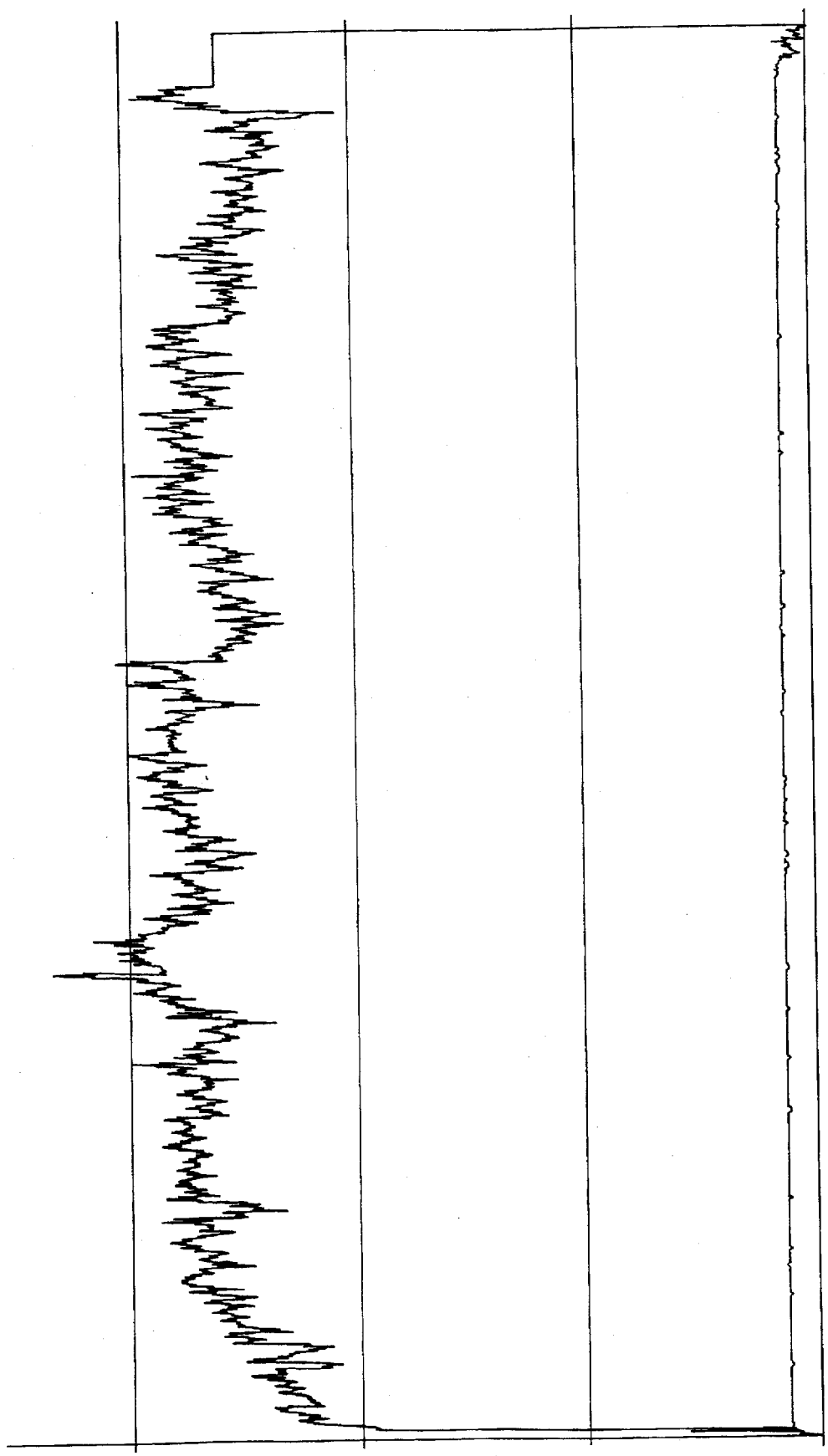

The "nearest of" approach has also been compared by us to an interpolation approach. FIGS. 11 and 12 show graphs of S/N ratio as presented in FIGS. 8 and 9, wherein four and eight monitor assembly readings are respectively taken per projection. The data was normalized using the number of monitor readings and interpolating the values for each data reading depending upon when each data reading was taken relative to the two nearest monitor readings in time. For example, with eight monitor readings taken at equal intervals for the 384 readings, beginning at reading 24, the normalization factor used at data reading 24 is the monitor reading 24. However, the normalized factor used at data reading 25 is 47 times the monitor reading at 24 added to 1 times the monitor reading at 72, with the resulting sum divided by the number of data readings between monitor readings (i.e. 48). Similarly, the normalized factor used at data reading 26 is 46 times the monitor reading at 24 added to 2 times the monitor reading at 72 with the resulting sum divided by 48, and so on. Interpolation is clearly much more computational than the nearest of technique with similar results, as can be seen by a comparison of FIG. 10 with FIGS. 11 and 12.

The foregoing thus provides for X-ray image data normalization in a filtered CT scanner of the type described that significantly reduces or overcomes the problems of the prior art. Image data signals associated with each view of a filtered CT scan are normalized so as to reduce the effects of time-dependent noise on the image data signals. The X-ray exposure level of a CT scanner is monitored during a scan so as to provide at least some correction for variations in the signal-to-noise ratio without placing large computational demands on the system so as to be preferable over the sliding window method described above. The image data signals associated with each projection of a filtered CT scan is normalized independent of the position of a patient under study or a patient support table within the field of view. The system therefore is an improvement over the system described in the Uno, et al. Patent. Further, by normalizing the data in accordance with the present invention so that the data readings are substantially independent of fluctuations of X-ray flux, the service life of X-ray tubes can be extended.

It should be noted that, according to the invention, any number of monitor readings per view that provides an acceptable S/N ratio over each view can be used, where acceptability is determined in part by context of use. In particular, four, eight, and sixteen monitor readings per view were illustrated, but any number such as six, seven, or twelve monitor readings per view can also be used. Factors that should be considered include image quality required, the number of data readings per projection and computational resources available in the CT scanner.

While the preferred embodiment has been described as a third generation CT scanner, the invention can be employed in other types of tomographic imaging systems, including fourth generation CT scanners.

Other modifications and implementations will occur to those skilled in the art without departing from the spirit and the scope of the invention as claimed. Accordingly, the above description is not intended to limit the invention except as indicated in the following claims.

What is claimed is:

1. An X-ray tomography apparatus of the type comprising: (a) an X-ray source for generating X-rays during a tomographic scan; (b) X-ray detection means, including a plurality of image data detectors, for detecting the X-rays emitted by said X-ray source and received by said data detectors along predetermined ray paths during a succession of projections of said tomographic scan, and for generating a plurality of image detector signals representative of the X-ray flux detected by said image data detectors during each of said projections; (c) tomographic scanning means for rotating at least the X-ray source about a scanned object during a tomographic scan; and (d) means for reading said image data detectors in a predetermined sequence for each of said projections, said apparatus further comprising:

monitor detector means for detecting X-rays generated by said source and received by said monitor detector means, and including means for providing a sequence of monitor measurement signals as a function of the X-ray flux detected by said monitor detector means at predetermined intervals during each of said projections; and means for normalizing each of the plurality of image detector signals acquired during each projection as a function of the monitor measurement signal occurring during the interval closest in time to when each said image detector signal is read.

2. The apparatus according to claim 1, wherein said monitor detector means includes means for providing a sequence of monitor measurement signals at equally spaced intervals during each projection.

3. The apparatus according to claim 1, wherein said monitor detector means includes means for providing a sequence of at least four measurement signals during each projection.

4. The apparatus according to claim 1, wherein said monitor detector means includes means for providing a sequence of at least eight measurement signals during each projection.

5. The apparatus according to claim 1, wherein said monitor detector means includes means for providing a sequence of at least sixteen measurement signals during each projection.

6. The apparatus according to claim 1, wherein the monitor detector means is positioned relative to said source so as to detect substantially unattenuated X-rays generated by said source.

7. The apparatus according to claim 1, wherein said ray paths of said projections of said scan define a scanning plane, the monitor detector means being positioned relative to said source outside said scanning plane.

8. The apparatus according to claim 1, wherein the means for normalizing the image detector signals includes means for determining which monitor measurement signal of the sequence of monitor measurement signals is closest in time to each image detector signal of the plurality of image detector signals.

9. The apparatus according to claim 1, further including means, disposed between said X-ray source and said monitor detector assembly, for defining an aperture so as to define an X-ray monitoring beam.

10. The apparatus according claim 9, wherein the aperture is diamond-shaped.

11. The apparatus according to claim 1, wherein the monitor detector assembly includes a plurality of detectors, each detector providing a monitor detector signal, and each monitor measurement signal representing the sum of the monitor detector signals.

12. A method of normalizing X-ray image data acquired during a CT scan by a system having an X-ray source for generating X-ray flux, a plurality of detectors for detecting X-ray flux from the source as the X-ray source rotates about a rotation axis through a plurality of projections, and means for reading the image detectors in accordance with a predetermined sequence once during each projection so as to provide a plurality of image detector signals for each projection, the method comprising the steps of:

monitoring the level of X-ray flux generated by said source during each of the projections so as to generate a preselected sequence of monitor measurement signals with respect to each of said projections; and normalizing each of the plurality of image detector signals acquired during each projection as a function of the monitor measurement signal occurring during the interval closest in time to when each said image detector signal is read.

13. The method according to claim 12, wherein the step of monitoring the level of X-ray flux includes the step of monitoring a substantially unattenuated portion thereof.

14. The method according to claim 12, wherein the step of normalizing includes the step of determining which monitor measurement signal of the sequence of monitor measurement signals is closest in time to each image detector signal of the sequence of image detector signals; and using only the monitor measurement signal of the sequence of monitor measurement signals that is closest in time to normalize each such image detector signal.

15. The method according to claim 12, wherein the step of normalizing each of the plurality of image detector signals acquired during each projection as a function of the monitor measurement signal occurring during the interval closest in time to when each said image detector signal is read includes the step of:

monitoring the level of X-ray flux generated by said source during each of the projections so as to generate a sequence of four monitor measurement signals with respect to each of said projections.

16. The method according to claim 12, wherein the step of normalizing each of the plurality of image detector signals acquired during each projection as a function of the monitor measurement signal occurring during the interval closest in time to when each said image detector signal is read includes the step of:

monitoring the level of X-ray flux generated by said source during each of the projections so as to generate a sequence of eight monitor measurement signals with respect to each of said projections.

17. The method according to claim 12, wherein the step of normalizing each of the plurality of image detector signals acquired during each projection as a function of the monitor measurement signal occurring during the interval closest in time to when each said image detector signal is read includes the step of:

monitoring the level of X-ray flux generated by said source during each of the projections so as to generate a sequence of sixteen monitor measurement signals with respect to each of said projections.

18. The method according to claim 12, wherein the projections all occur substantially along a scanning plane and the step of monitoring the level of X-ray flux generated by said source during each of the projections so as to generate a preselected sequence of monitor measurement signals with respect to each of said projections includes the step of:

monitoring the level of X-ray flux generated by said source outside the scanning plane so as to ensure that the monitoring function cannot interfere with acquisition of image data.

19. An X-ray tomography apparatus of the type comprising: (a) an X-ray source for generating X-rays during a tomographic scan; (b) X-ray detection means, including a plurality of image data detectors, for detecting the X-rays emitted by said X-ray source and received by said data detectors along predetermined ray paths during a succession of projections of a tomographic scan in a scanning plane so as to define a field of view, and for generating a plurality of image detector signals representative of the X-ray flux detected by said image data detectors during each of said projections; (c) tomographic scanning means for rotating at least the X-ray source about a scanned object during a tomographic scan; and (d) means for reading said image data detectors for each of said projections so as to generate image data for each projection, said apparatus further comprising:

monitor detector means, disposed outside said field of view, for detecting X-rays generated by said source during substantially the same time as when the X-ray detection means detects said X-ray flux during each of said projections, and including means for providing monitor measurement signals as a function of the X-ray flux detected by said monitor detector means during each of said projections; and means for normalizing said image data for each projection with monitor measurement signals acquired during that projection.

20. The apparatus according to claim 19, wherein the monitor detector means is positioned outside said scanning plane.

21. A method of normalizing data acquired during the scan of an object disposed within a field of view by a CT scanner comprising a source of X-rays, an array of detectors for detecting X-rays emitted by the source, means for rotating at least the source about a rotation axis so as to define ray paths between said source and said detectors for the projections of a scan and therefore define the field of view within a scanning plane of the scanner, and a monitoring detector assembly positioned to detect X-rays emitted by the source along at least one ray path outside the field of view, said method comprising the steps of:

measuring X-ray flux emitted by said source and detected by each of said detectors of said array and said monitoring detector assembly with a material providing a predefined amount of X-ray absorption disposed within the field of view so as to define initial detector measurements;

acquiring data during a scan of the object including the step of measuring X-ray flux emitted by said source and detected by each of said detectors of said array with the object disposed within the field of view so as to define X-ray flux projection measurements;

measuring the X-ray flux emitted by said source and detected by said monitoring detector assembly a plurality of times during the same time as each of said projection measurements are made so as to define monitor detector assembly measurements for each of said projections;

normalizing said data for each of said projections as a function of said initial detector measurements, and the corresponding X-ray flux projection measurements and said monitor detector assembly measurements measured during that projection.

* * * * *